United States Patent [19]
Chin

[11] Patent Number: 5,449,380
[45] Date of Patent: Sep. 12, 1995

[54] APPARATUS AND METHOD FOR ORGAN ABLATION

[75] Inventor: Albert K. Chin, Palo Alto, Calif.

[73] Assignee: Origin Medsystems, Inc., Menlo Park, Calif.

[21] Appl. No.: 122,394

[22] Filed: Sep. 17, 1993

[51] Int. Cl.⁶ .............................................. A61F 7/12
[52] U.S. Cl. ................................ 607/105; 606/28; 604/96
[58] Field of Search ................ 607/96, 104–106; 604/93, 96–97, 98–99; 606/27–31

[56] References Cited

U.S. PATENT DOCUMENTS

| 899,477 | 9/1908 | Williams . | |
|---|---|---|---|
| 2,190,383 | 2/1940 | Newman . | |
| 2,190,384 | 2/1940 | Newman . | |
| 2,734,508 | 2/1956 | Kozinski . | |
| 3,460,538 | 8/1969 | Armstrong . | |
| 3,848,607 | 11/1974 | St. Clair . | |
| 3,918,443 | 11/1975 | Vennard et al. . | |
| 3,924,628 | 12/1975 | Droegemueller et al. . | |
| 4,018,230 | 4/1977 | Ochiai et al. . | |
| 4,022,215 | 5/1977 | Benson . | |
| 4,878,495 | 11/1989 | Grayzel . | |
| 4,949,718 | 8/1990 | Neuwirth et al. | 607/105 |
| 5,084,044 | 1/1992 | Quint | 607/105 X |
| 5,100,388 | 3/1992 | Behl et al. | 604/113 |
| 5,105,808 | 4/1992 | Neuwirth et al. . | |
| 5,116,305 | 5/1992 | Milder et al. | 600/18 |
| 5,159,925 | 11/1992 | Neuwirth et al. . | |
| 5,188,602 | 2/1993 | Nichols | 604/96 X |
| 5,195,965 | 3/1993 | Shantha | 607/105 X |
| 5,242,390 | 9/1993 | Goldrath | 607/105 X |
| 5,257,977 | 11/1993 | Eshel | 604/96 X |
| 5,308,327 | 5/1994 | Heaven et al. | 604/96 |

FOREIGN PATENT DOCUMENTS

WO92/12694 8/1992 WIPO .

Primary Examiner—Angela D. Sykes
Attorney, Agent, or Firm—Limbach & Limbach

[57] ABSTRACT

An apparatus and method for cauterizing the endometrial tissue of the uterus includes an inflatable balloon mounted to the end of a cannula and spring members which shape the balloon to approximate the bicornual shape of the uterus. A heating coil heats a saline solution to approximately 190°–210° F. and a pump circulates the saline solution through the cannula and inflates the balloon. The inflated balloon contacts substantially all of the intrauterine surface and is held in contact with the surface for 5 to 7 minutes until the tissue has been necrosed. A fiberoptic scope is used to monitor balloon placement and cauterization effect.

12 Claims, 3 Drawing Sheets

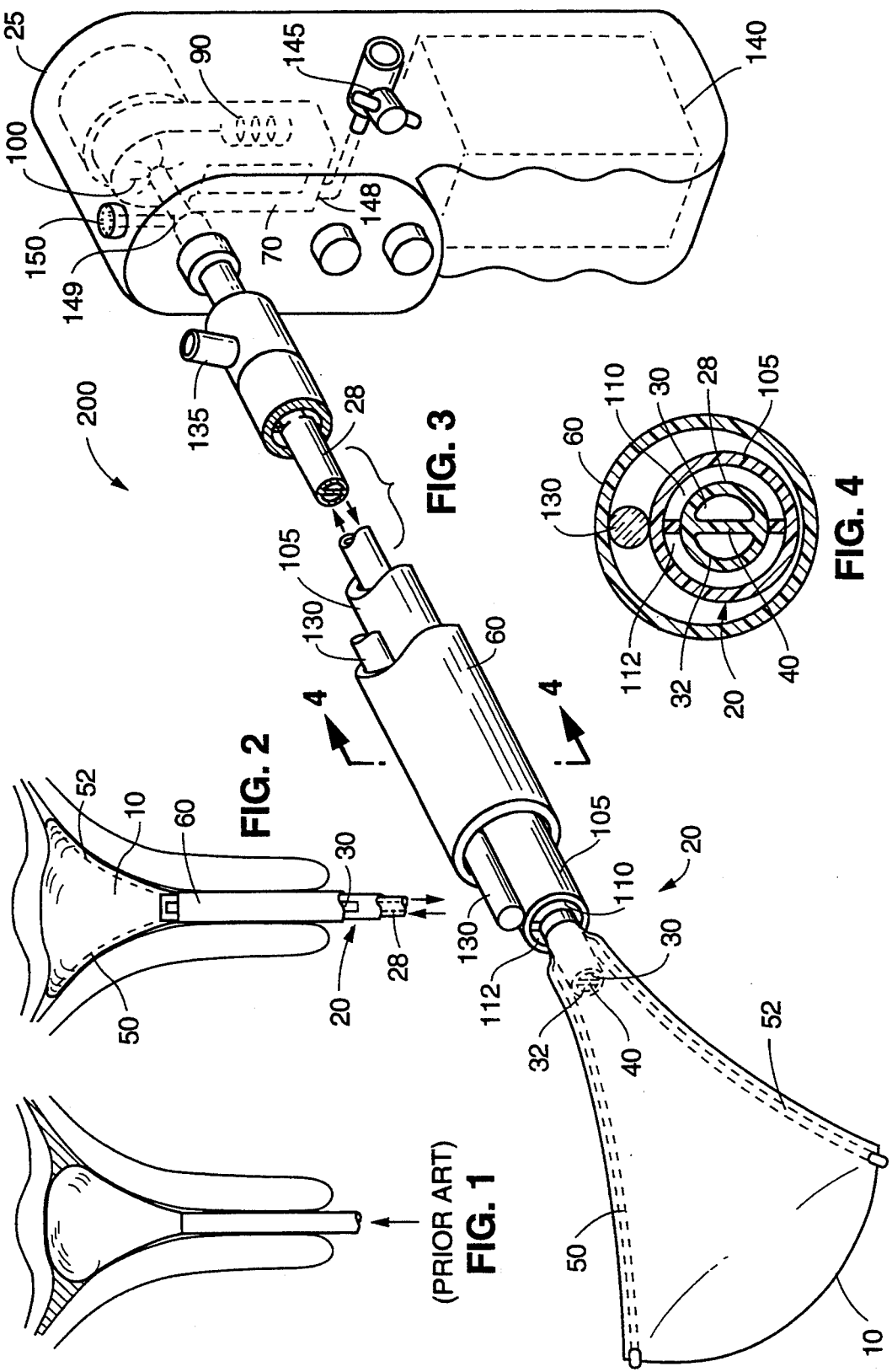

APPARATUS AND METHOD FOR ORGAN ABLATION

FIELD OF THE INVENTION

The present invention relates to an apparatus and method for necrosing the lining of a body cavity and, more particularly, for doing so using a balloon shaped to conform to the shape of the organ.

BACKGROUND OF THE INVENTION

A tissue ablator is a device used to cauterize, or induce necrosis of, living tissue. Intrauterine tissue ablators are useful for treating menorrhagia and metrorrhagia, excessive bleeding conditions sometimes evidenced by pain or discomfort.

Ablation is usually accomplished by thermal or cryogenic treatments. One thermal procedure involves treatment of the tissue with a laser or electrocautery device. A physician using this procedure for uterine ablation must "paint" the intrauterine surface with the laser beam or electrocautery probe, making it difficult to uniformly treat the entire intrauterine area. Incomplete treatment results in continued bleeding or discomfort. Also inherent in the laser and electrocautery techniques is the risk that an area of the tissue surface will be punctured from prolonged exposure to the beam or probe.

Another method of organ ablation involves an inflatable bladder which is inserted into the organ and inflated with a thermal or cryogenic substance. The inflated bladder contacts the surrounding tissue and the extreme temperature of the thermal or cryogenic substance in the balloon causes the tissue to necrose.

One such device intended for intrauterine cauterization is disclosed in U.S. Pat. No. 4,949,718. An inflatable bladder located at the end of a cannula is inserted into the uterus. A liquid medium is used to fill the bladder, causing it to inflate inside the organ. Heating coils located inside the bladder heat the medium to temperatures of 1900° to 215° F., temperatures known to induce necrosis of endometrial tissue. The temperature of the medium is maintained until the tissue surfaces in contact with the bladder are cauterized. U.S. Pat. No. 5,105,808 describes an intrauterine cauterizing method utilizing the device just described.

This device suffers from several disadvantages. Firstly, the bladder used is substantially spherical, whereas the uterus is bicornuate in shape. The cornual regions of the uterus therefore remain untreated because the spherical bladder does not make contact with them (see FIG. 1). Moreover, the device does not allow the physician to visually verify that the bladder has been properly placed or that the entire endometrial surface has been sufficiently cauterized. The patient may continue to suffer bleeding or discomfort as a result of incomplete cauterization. Finally, the heating element is located inside the body during treatment. The heating coil reaches temperatures much higher than the fluid temperature and its placement in the bladder creates the risk that the patient may be burned.

SUMMARY OF THE INVENTION

The present invention cauterizes tissue by circulating a heated fluid through a balloon which is inserted into a hollow organ on the tip of a cannula. The apparatus includes an inflatable balloon attached to the distal end of a cannula, an inflation means for circulating an inflation fluid through the cannula and the balloon, and a heating means for heating the inflation fluid to an elevated temperature. The balloon is mechanically shaped to approximate the shape of the organ.

The present invention provides several advantages over the prior art. A primary advantage is that conforming the balloon to the approximate shape of a uterus allows the entire surface of the uterus, including the cornual regions, to be contacted and treated by the balloon (FIG. 2).

DESCRIPTION OF THE DRAWINGS

FIG. 1 is a cross-sectional side elevation of a uterus showing an inflated spherical balloon encountered in the prior art.

FIG. 2 is a cross-sectional side elevation of a uterus showing an inflated balloon of a tissue ablation apparatus according to the present invention.

FIG. 3 is a partially cut away side perspective of the tissue ablation apparatus.

FIG. 4 is a cross-sectional view of a cannula taken on the plane designated by 4—4 in FIG. 3.

DETAILED DESCRIPTION

Figure 5:
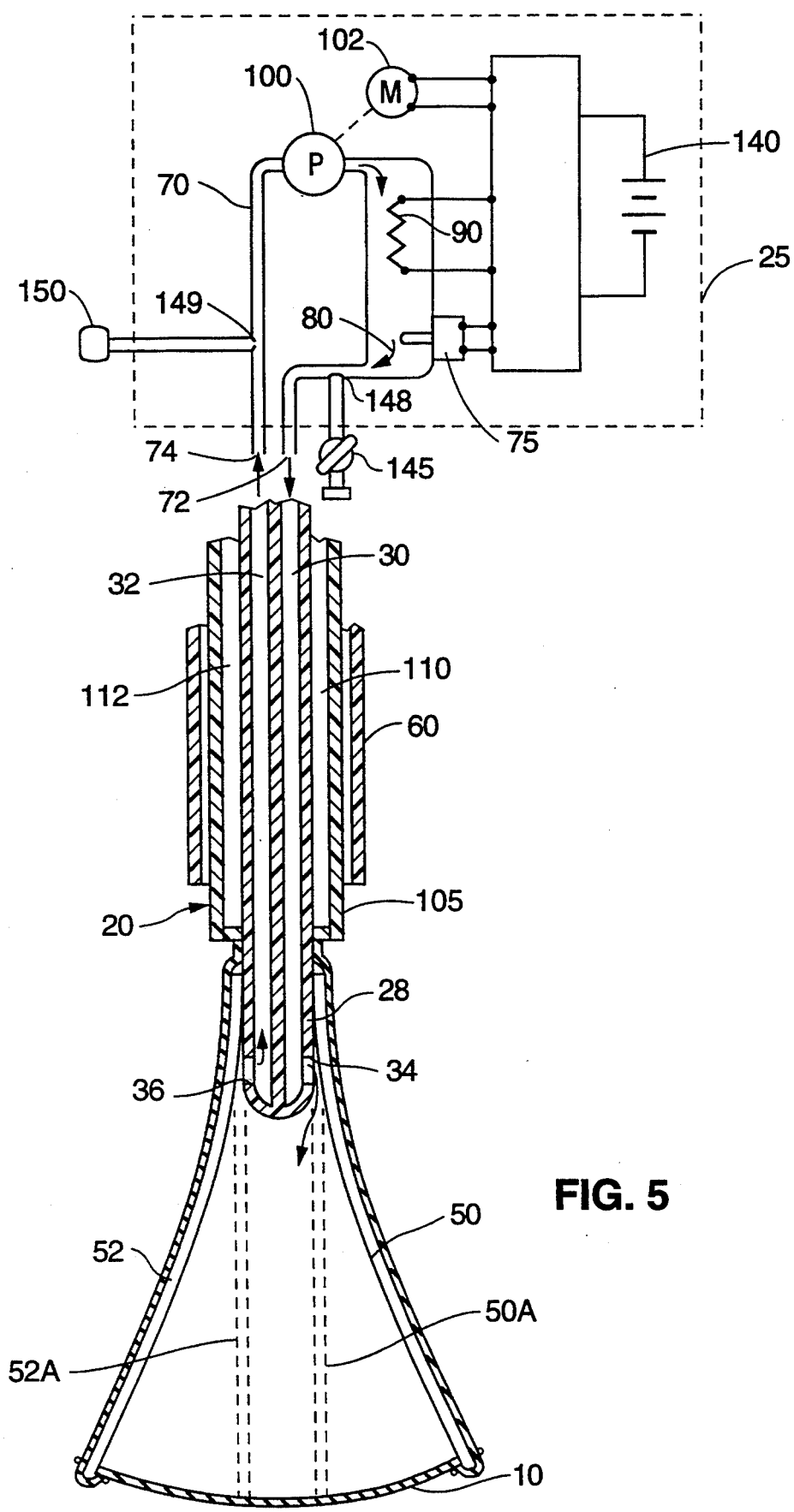
FIG. 5 is a cross-sectional side elevation of the tissue ablation apparatus with parts broken away and the heater shown in schematic representation.

Referring to FIG. 3, an organ tissue ablator 200 according to the present invention is comprised of an inflatable balloon 10 which is sealed around the distal end of a cannula 20. A handle 25, having knobs 42 for controlling inflation and heating functions, is attached to the proximal end of the cannula 20.

FIG. 3 shows a side perspective of a longitudinal portion of the device, including the cannula 20. At the core of the cannula 20 is a flow tube 28 which is comprised of a pair of lumen 30, 32. The lumen are sealed from one another by a wall 40 and extend the entire length of the cannula 20. Surrounding the flow tube 28 within the cannula 20 is an insulation tube 105 which consists of a pair of air-filled channels 110, 112 (See FIG. 4).

Figure 6:
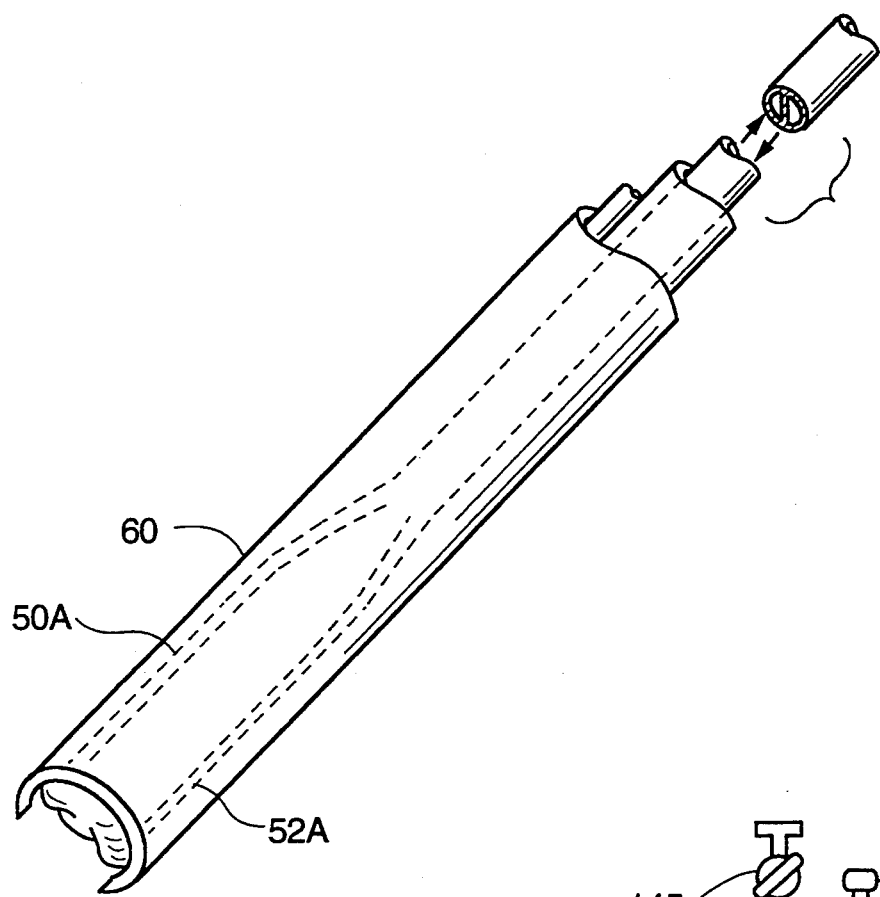
FIG. 6 is a partially cut away side perspective of the distal portion of a tissue ablation apparatus having a tubular sheath positioned in the distal position.

A slidably mounted tubular sheath 60 surrounds the cannula 20. The tubular sheath 60 can be manually moved between a proximal position as shown in FIG. 3 and a distal position which is shown in FIG. 6. A fiberoptic tube 130 is positioned between the tubular sheath 60 and the cannula 20 to provide visual access to the balloon location via a fiberoptic scope 135.

FIG. 4 shows a cross-sectional view of the cannula 20, fiberoptic tube 130, and tubular sheath 60 taken along the plane designated by 4—4 in FIG. 3. FIG. 5 shows a cross-sectional side elevation of a tissue ablation apparatus and illustrates the positioning of the flow tube 28 inside the balloon 10. Each of the lumen 30, 32 has a side port 34, 36 which allows fluid to flow from the outward lumen 30 into the balloon 10 and from the balloon 10 into the return lumen 32.

Handle 25 is located at the proximal end of the cannula 20. Inside the handle 25 is a fluid path 70 having an outward channel 72 and a return channel 74 which connect to the outward lumen 30 and the return lumen 32 respectively. Two holes 148, 149 pass from the fluid path 70 and through the handle 25. One hole connects with a porous plug 150 and the other leads to a stopcock 145.

The fluid path 70 is filled with an inflation fluid 80 which may be a liquid or a gas. The preferred embodiment utilizes approximately 30–40 cc of a saline solution.

A heating coil 90 situated within the fluid path 70 heats the inflation fluid 80 to approximately 190°–220° F., a temperature adequate to effect cauterization of endometrial tissue. A thermostatic temperature regulator 75 electronically maintains the heating coil 90 at the temperature necessary to keep the inflation fluid 80 at the cauterization temperature.

A pump 100, driven by a battery powered motor 102, causes the inflation fluid 80 to fill and inflate the balloon 10. The fluid flow through the fluid path 70 and lumen 30, 32 is indicated by arrows in FIG. 5. The pump 100 circulates the fluid from the fluid path 70 to the balloon 10 through the outward lumen 30 and back to the fluid path 70 through the return lumen 32. The insulation tube 105, which surrounds the lumen 30, 32, limits the amount of heat transferred from the heated fluid in the lumen 30, 32 to the exterior of the cannula 20.

A battery 140, located in the handle 25, provides the power necessary for the heating coil 90 and the motor 102.

A pair of spring members 50, 52 is mounted to the distal end of the cannula 20, inside the balloon 10. In their normal outwardly biased extended position the spring members 50, 52 are arcuate in shape, arching outward from the longitudinal axis of the cannula 20. The spring members 50, 52, can be restrained in a substantially straight contracted position, designated 50a and 52a and indicated by dotted lines in FIG. 5, wherein they are substantially parallel to the longitudinal axis of the cannula 20.

FIG. 6 shows the distal end of the cannula 20 with the tubular sheath 60 in the distal position. When in its distal position, the tubular sheath 60 surrounds the balloon 10 and spring members 50, 52 and restrains the spring members 50, 52 to their straight contracted position. When moved to its proximal position, the tubular sheath 60 no longer restrains the spring members 50, 52, allowing them to spring into their open, arcuate positions as shown in FIGS. 3 and 5.

Use of the preferred embodiment will next be described.

A local anesthetic is administered and the cervix is dilated. Air is purged from the device by partially filling the system with saline solution. This partial filling is performed prior to insertion of the device into the uterus, with the tubular sheath 60 held in the distal position to prevent the balloon from inflating.

Figure 7:
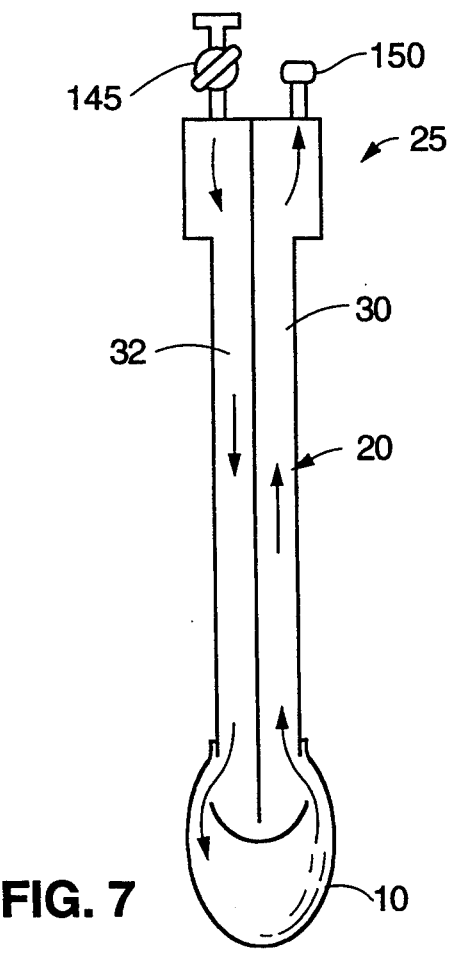
FIG. 7 is a schematic representation of the tissue ablation apparatus illustrating the process of filling a cannula with inflation fluid.

Referring to FIG. 7, the device is held vertically with the handle 25 on top and the balloon 10 on the bottom to facilitate purging. Saline solution is slowly introduced through the stopcock 145 using a syringe (not shown) until no additional fluid will be accepted by the system. During filling, the fluid enters the flow path 70 (not shown in FIG. 7) and follows the path indicated by arrows in FIG. 7, pushing excess air out through the porous plug 150. The pores in the porous plug 150 are large enough to allow air to exit the system, but are small enough to prevent fluid from exiting. The system will therefore stop accepting fluid through the stopcock 145 when the system is full of fluid and all air has been purged. A one-way valve (not shown) is preferably located between the porous plug 150 and the flow path 70 to prevent air from entering the system after purging.

The cannula is next inserted into the uterus with the tubular sheath 60 positioned in the distal position, such that the balloon 10 and springs 50, 52 are restrained by the tubular sheath 60 as shown in FIG. 6. The sheath 60 is then moved to the proximal position, allowing the springs 50, 52 to release into their resting positions as shown in FIG. 5. The positioning of the balloon and springs may be observed through the fiberoptic scope 135.

Once the balloon 10 has been properly positioned, the system is filled completely with saline solution and the balloon 10 is inflated. Using a syringe, fluid is introduced through the stopcock 145 until the balloon is inflated. The stopcock is then closed. Once inflated, the bicornate shaped balloon makes contact with the uterine walls as shown in FIG. 2.

The battery-powered pump 100 and heating coil 90 are next switched on. The fluid circulates into and out of the inflated balloon 10 via the lumen 30, 32. The heating coil 90 located in the fluid path 70 heats the fluid to approximately 210° F. and the temperature is maintained by the thermostatic controls 75.

The apparatus is kept in place for approximately 5 to 7 minutes for effective cauterization. By looking through the fiberoptic scope 135, the physician can evaluate whether additional cauterization time is needed.

The system is emptied of fluid after treatment by attaching the syringe to the stopcock, opening the stopcock 145, and siphoning the fluid from the system by withdrawing the barrel of the syringe.

Conclusion

The present invention is described in relation to the preferred embodiment but is limited only in terms of the language of the appended claims.

I claim:

1. An apparatus for ablating tissue in a uterus, comprising:
   (a) a cannula having a proximal end and a distal end;
   (b) an inflatable balloon attached to the distal end of the cannula;
   (c) spring members attached to the distal end of the cannula and having free ends engaged with the balloon to conform the balloon to the shape of the uterus;
   (d) inflation means for circulating an inflation fluid through the cannula and into the balloon and for inflating the balloon;
   (e) heating means for heating the inflation fluid to an elevated temperature; and
   (f) purging means for removing air from the balloon and cannula without significantly removing inflation fluid from the balloon and cannula.

2. The apparatus of claim 1 wherein the cannula has a longitudinal axis and wherein the spring members have a contracted position in which the spring members are substantially parallel to the longitudinal axis of the cannula and an extended position in which the spring members arch away from the longitudinal axis of the cannula to conform the balloon to a substantially bicornuate uterus shape and to direct portions of the balloon into cornual regions of the uterus.

3. The apparatus of claim 2 further comprising:

restraining means for holding the spring members in the contracted position; and releasing means for releasing the spring members for movement from the contracted position to the extended position.

4. The apparatus of claim 3 wherein the restraining means and the releasing means comprise a tubular sheath positioned around the cannula, the tubular sheath slidably mounted in a longitudinal direction and having a distal position wherein the tubular sheath is disposed around the balloon and spring members and restrains the spring :members in their contracted position, and a proximal position wherein the tubular sheath is positioned adjacent to the balloon and spring members and releases the spring members into their extended position.

5. The apparatus of claim 1 further comprising insulating means for preventing transfer of heat between the inflation fluid and the exterior of the cannula.

6. The apparatus of claim 1 wherein the invention further comprises two lumen located within the cannula, the lumen extending longitudinally from the proximal end of the cannula to the distal end of the cannula, one lumen supplying heated fluid to the balloon and the other lumen returning fluid from the balloon to the heating means.

7. The apparatus of claim 1 further comprising a scope extending from the balloon to the proximal end of the cannula.

8. The apparatus of claim 1 further comprising:

a battery for providing power to the inflation means and heating means, the battery positioned inside the handle.

9. An apparatus for ablating tissue in an organ comprising:

(a) a cannula having a proximal end, a distal end, a throughbore, and a hole formed through a wall of the cannula, the hole being in fluid communication with the throughbore;

(b) an inflatable balloon attached to the distal end of the cannula;

(c) shaping means for mechanically shaping the balloon to approximate the shape of the organ;

(d) inflation means for circulating an inflation fluid through the cannula and into the balloon and for inflating the balloon; and (e) heating means for heating the inflation fluid to an elevated temperature; and (f) purging means comprising a porous plug positioned in the hole, the plug having pores sized to allow passage of air therethrough and to prevent inflation fluid from passing therethrough.

10. The apparatus of claim 9 further comprising a handle connected to the proximal end of the cannula, said handle having a hole therein in fluid communication with the cannula and wherein the purging means includes a porous plug positioned in the hole.

11. The apparatus of claim 10 wherein the heating means is within the handle.

12. The apparatus of claim 10 wherein the handle has a second hole therein in fluid communication with the cannula and a valve connected to the second hole.

* * * * *